Figure 1:
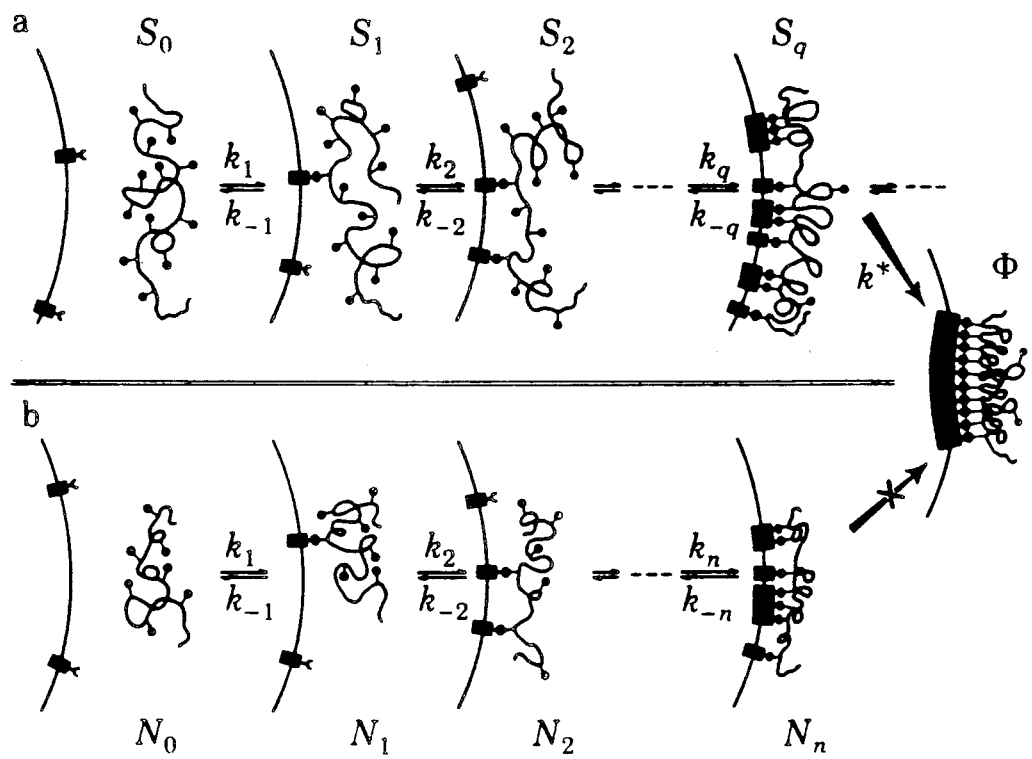

United States Patent [19]
Dintzis et al.

[11] Patent Number: 5,126,131

[45] Date of Patent: Jun. 30, 1992

[54] THERAPEUTIC SUPPRESSION OF SPECIFIC IMMUNE RESPONSES BY ADMINISTRATION OF ANTIGEN-COMPETITIVE CONJUGATES.

[75] Inventors: Howard M. Dintzis; Renee Z. Dintzis, both of Baltimore, Md.

[73] Assignee: The Johns Hopkins University, Baltimore, Md.

[21] Appl. No.: 248,293

[22] Filed: Sep. 21, 1988

Related U.S. Application Data

[63] Continuation of Ser. No. 869,808, May 29, 1986, abandoned, which is a continuation of Ser. No. 460,266, Jan. 24, 1983, abandoned.

[51] Int. Cl.$^5$ ............................................ A61K 39/395
[52] U.S. Cl. ........................................ 424/88; 424/89; 424/90; 424/91; 424/92; 514/2; 514/8; 514/10; 514/21; 530/403; 530/402; 530/404; 530/405; 530/406; 530/807; 530/810; 530/813
[58] Field of Search ........................ 424/88, 89, 90, 91, 424/92; 530/350, 387, 388, 389, 390–393, 401–406, 806, 808; 514/2, 8, 10, 11, 12, 21

[56] References Cited

U.S. PATENT DOCUMENTS

| | | |
|---|---|---|
| 3,794,630 | 2/1974 | Mullan . |
| 3,869,546 | 3/1975 | Lund . |
| 3,919,411 | 11/1975 | Glass . |
| 4,140,679 | 2/1979 | Malley . |
| 4,191,668 | 3/1980 | Katz . |
| 4,253,995 | 3/1981 | Katz . |
| 4,261,973 | 4/1981 | Lee . |
| 4,310,514 | 1/1982 | Durette . |

OTHER PUBLICATIONS

Desaynard, C. et al, Eur. J. Immunol, vol. 5, pp. 541–545 (1975).
Lui, F. et al, Proc. Natl. Acad. Sci, U.S.A., vol. 76(3), pp. 1430–1434 (1979).
Peacock, J. S. et al., J. Immunology, vol. 127(3) pp. 900–906 (1981).
Immunological Reviews, vol. 50, *Unresponsivenes To Haptenated Self Structures*, Copenhagen (1980).
Immunological Reviews, vol. 43, *Mechanism of B Lymphocyte Tolerance*, Copenhagen (1979).
Brown, H. M. et al., Acta Allergolagica, vol. 31, pp. 22–34 (1976).
Feldmann, M., J. Exper. Med, vol. 135, pp. 735–753 (1972).
Feldmann, M. et al. *Extracellular Matrix Influence on Gene Expression*, Academic Press, London (1975).
Perelson, A. A. et al. in *Paradoxes in Immunology*, Hoffman, G. W. et al. eds, CRC Press, Boca Raton, Fla. (1986), pp. 199–214.
Dintzis et al, "Molecular Determinants of Immunogenicity: The Immunon Model of Immune Response", Proc. Natl. Acad. Sci. U.S.A., vol. 73, No. 10, pp. 3671–3675, Oct. 1976.
"Specific Cellular Stimulation in the Primary Immune Response: A Quantized Model" by B. Vogelstein et al, Proc. Natl. Acad. Sci, U.S.A. vol. 79, pp. 395–399, Jan. 1982.
"Specific Cellular Stimulation in the Primary Immune Response: Experimental Test of a Quantized Model" by R. Z. Dintzis et al, Proc. Natl. Acad. Sci, U.S.A., vol. 79, pp. 884–888, Feb. 1982.
"Studies on the Immunogenicity and Tolerogenicity of T-Independent Antigens", by Renee Z. Dintzis et al, The Journal of Immunology, vol. 131, No. 5, Nov. 1983.
Chiorazzi et al, Proc. Natl. Acad. Sci. U.S.A., vol. 73, No. 6, pp. 2091–2095, Jun. 1976.

*Primary Examiner*—Esther L. Kepplinger
*Assistant Examiner*—Jeff Kushan
*Attorney, Agent, or Firm*—Cushman, Darby & Cushman

[57] ABSTRACT

Undesired immune responses are suppressed by administering a nonimmunogenic material which comprises one or more haptens or epitopes corresponding to the antigen which causes the undesired immune response, the number and spacing of the haptens or epitopes being insufficient to trigger an immune response but sufficient to inhibit it. Also disclosed is an improved vaccine from which low molecular weight suppressive polymer has been removed.

6 Claims, 3 Drawing Sheets

THERAPEUTIC SUPPRESSION OF SPECIFIC IMMUNE RESPONSES BY ADMINISTRATION OF ANTIGEN-COMPETITIVE CONJUGATES.

The invention described herein was made in the course of work under a grant or award from the Department of Health and Human Services.

This is a continuation of application Ser. No. 06/869,808, filed May 29, 1986, now abandoned, which is a continuation of Ser. No. 460,266, which was abandoned upon the filing hereof filed Jan. 24, 1983, now abandoned.

The present invention is concerned with the therapeutic suppression of undesirable immune responses. The invention is also concerned with the provision of vaccines of improved effectiveness.

It is well known that the immune system of living animals synthesizes antibodies in response to the presence of a foreign substance (i.e. an antigen) in the body. These antibodies have a specific affinity for the foreign substance which causes the antibodies to be synthesized. It is understood that such synthesis is triggered by binding between the antigen and receptors for the antigen on, or extending from, the surface of B-lymphocytes. This contact causes the specific cells involved to begin dividing and creating antibodies which, under normal circumstances, defend the animal body against the specific antigen which triggered the antibody formation.

There are, however, certain situations where the body provides an immune response which is undesirable. Such responses include, for example, allergic reactions which are characterized by the production of IgE antibodies to extrinsic antigens, and autoimmune diseases where antibodies are produced against self-antigens so that, in a sense, the immune system is working against the body rather than in support of it. Organ transplants, such as a replacement kidney or liver, present other specific situations of undesired immune response where the transplant may be rejected by the body by the generation of antibodies which, in essence, attack the transplant as foreign to the body.

In the past allergic reactions have generally been treated by repeated small stimulatory doses of antigen which are administered in the expectation that high resulting levels of specific antibody of type IgG will attenuate the deleterious inflammatory effects of specific antibodies of the class IgE. Disadvantages of this prior treatment include danger of anaphylactic reaction to the stimulatory doses used and the inconvenience and discomfort caused by frequent injections and increasing doses of allergen.

The treatment of autoimmune diseases, e.g. multiple sclerosis or myasthenia gravis, varies with the type of autoimmune disease. However, such treatments which exist do not in general encompass specific immunological principles. Steroids and immuno-suppressive reagents may be used to suppress the immune response in general. However, these agents are usually non-specific and they produce undesirable toxic side-effects. They may also cause general bone marrow depression and/or increased susceptibility to severe infection due to their non-specific effect on immune response.

There is, therefore, a real need for methods which can be used to effectively suppress undesired immune responses of the type indicated while obviating at least some of the disadvantages and problems encountered with prior treatments. The principal object of the invention is to provide such a method. Other objects, including the provision of new and improved vaccines, will also be hereinafter evident.

BROAD DESCRIPTION OF THE INVENTION

Broadly speaking, the method of the invention comprises administering to a subject suffering from an undesired immune response an effective amount of a non-immunogenic material which carries a relatively small number of antigenic domains (i.e. "epitopes" or "haptens") which correspond to the antigen, e.g. the allergen or self-antigen which causes the allergy or autoimmune disease responsible for the undesired response. The haptens bind to cell antigen receptors specific to the indicated haptens and, provided the number of such haptens per carrier entity is below an ascertainable threshold limit so as to avoid the formation of a stimulatory cluster of connected antigen receptors, as discussed below, the administered material serves to suppress the specific immune response.

Stated another way, the invention contemplates the therapeutic suppression of a specific undesired immune response by the administration of specific forms of antigen of controlled chemistry designed to competitively bind to the antigen receptors, thereby preventing stimulatory antigen from causing the undesired response. The administered material operates by specifically suppressing the production of antibody to a particular allergen or self-antigen which is of concern, without compromising or damaging the general immune competence of the body. The method of the invention, therefore, deals only with a specific immune response and not with the immune response in general.

According to the invention, the offending antigen, e.g. allergen or self-antigen, is identified so as to provide a molecular entity which contains a single or very small number of antigenic domains (epitopes or haptens). An appropriate number of these molecular entities containing the desired number of epitopes or haptens is then bonded by covalent linkage to a biologically inert substance, e.g. a polymer, or liposome, which functions as a carrier for the antigenic domains or epitopes. The carrier, with the thus-added epitopes or haptens is then administered to the subject in need of treatment to control the undesired immune response. In this connection, it will be appreciated that the carrier needs to be biologically inert only in the present context but may nor may not be inert with respect to other biological functions.

The success of the invention is based on the dual findings that (a) there is a threshold number and spacing of haptens on a polymer carrier or the like which are essential to form a cluster of connected antigen receptors to stimulate antibody formation and (b) the presence of molecules containing a sub-threshold number of haptens, not only will not stimulate antibody formation but more significantly, for present purposes, suppresses antibody formation by competing for the available antigen receptors. The present method utilizes this suppression finding (b) to control or eliminate the undesired immune response by suppressing antibody response.

The concept of there being a threshold limit as to the number and spacing of haptens to obtain an immunogenic response is disclosed in a 1976 paper we have co-authored with Vogelstein, entitled "Molecular Determinants of Immunogenicity: The Immunon Model of Immune Response", Proc. Nat'l Acad. Sci. USA, Vol. 73, No. 10, pages 3671-3675, October 1976. In that paper we have described some of our earlier work in which the immunological response in vivo to a series of size-fractionated linear polymers of acrylamide substituted with dinitrophenyl (Dnp) hapten, was measured in mice. The paper reports that a sharp threshold was observed in immunogenic response elicited by various polymer preparations. In particular, all polymers with less than 12 to 16 appropriately spaced hapten group per molecule were nonimmunogenic, while those polymers with greater than this number were fully immunogenic. The results indicate that the immunological response at its most elementary level is quantized, i.e., a minimum specific number of antigen receptors (approximately 12 to 16 for the work reported) must be connected together as a spatially continuous cluster, an immunon, before an immunogenic signal is delivered to the responding cell.

Our 1976 paper also discloses that the nonimmunogenic polymers were suppressive of the action of immunogenic polymer towards triggering the de novo immune response in non-immunized animals. Apparently the suppressive effect of the nonimmunogenic polymers is due to the fact that the haptens present compete for cell receptors and prevent the cluster (or immunon) formation needed to trigger the immune response. In other words, there is a competitive effect from the "sub-threshold" polymers, which bind receptors in clusters that are too small to act as immunons and consequently reduce the number of free receptors available to the immunogenic polymer molecules so that these latter molecules cannot find enough antigen receptors to form the clusters or immunons, or necessary number of these, to trigger the cell to antibody production. Regardless of the theory involved, however, it is evident that the non-immunogenic polymers which carry less than the number of appropriately spaced haptens which are essential to stimulate the immune response, function to suppress the response. These nonimmunogenic molecules are, therefore, suppressive of the stimulatory antigen. Accordingly, injection of very small amounts of these non-immunogenic molecules results in a profound and long-lasting suppression of immune response.

While our 1976 paper discloses the suppressive action of the non-immunogenic polymer on the immunogenic effect of immunogenic Dnp-polyarylamide, the paper does not disclose, and it is not obvious therefrom, that the suppressive effect of a non-immunogenic polymer carrying less than the threshold number of haptens can be used with advantage in the treatment of allergies or autoimmune diseases by suppressing or turning off the undesired immune response and resultant antibody formation. The 1976 paper also does not disclose the possibility of using proteins or liposomes as carriers for epitopes.

The suppressive effect of non-immunogenic polymers on the immunogenic response of immunogenic polymers is further described in two additional papers which we have recently co-authored entitled "Specific Cellular Stimulation in the Primary Immune Response: A Quantized Model", Proc. Nat'l Acad. Sci. USA, Vol. 79, pp. 395-399, January 1982, and "Specific Cellular Stimulation in the Primary Immune Response: Experimental Test of a Quantized Model", Proc. Nat'l Acad. Sci. USA, Vol. 79, pp. 884-888, February 1982. The first of the 1982 papers referenced above indicates that a general theory for the initial phase of T cell-independent immune response is derived from elementary physical-chemical considerations and from the premise that response entails a quantized linkage of cell surface receptors. The theory leads to the construction of explicit antigen dose-response and antigen dose-suppression curves, to the calculation of intrinsic affinities for receptors, and to the deduction that receptors are divalent in character. The theory may be applicable to other cell surface phenomena wherein requirements for stimulation and suppression are equivalent to those found in the immune system. The second of the above-reference 1982 papers includes dose-response and dose-suppression curves measured for the primary immune response in mice, in vivo and in vitro, by using size fractionated linear polymers of acrylamide substituted with hapten. The results are in general agreement with a simple theory based on the premise that the specific primary immunological response is quantized at some fundamental and limiting step, requiring a minimum number of linked antigen receptors for response. The contents of these 1982 papers and our 1976 paper are incorporated herein by reference.

It will be appreciated that it is essential, for the practice of the invention, to first determine the antigen (e.g. allergen or self-antigen) which causes the undesired immune response. This means that the allergen or self-antigen, if not already known, must be identifiable. Once this is done, it is possible to construct the non-immunogenic molecule by known means to incorporate a selected number of haptens or epitopes corresponding to the allergen or self-antigen on an appropriate biologically inert synthetic or natural carrier material such as polyacrylamide, polyvinylpyrolidone, dextran, or like polymer, with less than the number of haptens or epitopes essential to trigger the immune response. Alternatively, the carrier may be a relatively non-immunogenic self-protein such as human serum albumin or gamma globulin or a liposome of appropriate composition and size (e.g. egg lecithin blended with an appropriate proportion of cholesterol and sonicated vigorously into the small size range of 250-400 Å). As noted earlier, administration of the resulting molecule, e.g. by injection, results in binding of the haptens to the antigen receptor sites of the appropriate B-lymphocytes in a way which prevents or reduces the formation of the large receptor clusters essential to trigger the undesired immune response.

The invention is thought to be broadly applicable to the treatment of any allergy or autoimmune disease where the responsible allergen or self-antigen is known or identifiable. Obviously not all such allergens or self-antigens have as yet been identified or isolated. On the other hand, enough of these allergens or self-antigens have already been identified to enable the useful construction of molecules which are suppressive to the undesired immune response, according to the invention. It has been demonstrated that an ongoing immune response to the hapten, Dnp, can be suppressed by subsequent injections of a sub-immunogenic Dnp-linear polyacrylamide preparation. The suppressive polymer used was of about 40,000 molecular weight. It was excreted relatively slowly from the body, and contained 11 Dnp groups per molecule. These groups were of sufficient number and density (about 100 Å apart) to nonproductively bind cell-surface receptors and thus prevent formation of an immunogenic signal.

Correspondingly, it is believed that an ongoing immune response to an allergen or a self-antigen can be inhibited by the synthesis and injection of similar appropriate sub-immunogenic molecules as described below.

It will be appreciated that the number and spacing of the haptens on the carrier can be widely varied and will depend on other factors, e.g. the antigen involved and the carrier employed. However, the optimum number and spacing for a particular hapten or epitope can be determined without undue experimentation by simple tests on experimental animals such as mice, rats, rabbits or guinea pigs, using the selected polymer and hapten. Since the desired suppressive effect appears to be based on competition for the cell receptors, it is usually preferred to uses a number of the haptens which is relatively close to the immunogenic threshold limit rather than a substantially lower number. For example, if the immunogenic threshold limit for a particular antigen is determined to be about 12-16 haptens spaced 100-200 angstroms apart along a polymer chain, a preferred non-immunogenic polymer could have 8-10 similarly spaced haptens. Less than this number could also be used although it should be expected that, in most cases, the results would not be as effective towards suppressing the immune response.

It will be evident from the foregoing that it is essential in each case to determine the threshold limit, in terms of the number and spacing of haptens, necessary to obtain an immunogenic effect based on the particular carrier which is used and the specific antigen involved. This can be determined using the process described in our 1976 paper. Once the threshold number and spacing are determined, it is a straightforward matter to construct the corresponding non-immunogenic polymer molecule or the equivalent with the sub-threshold number of haptens or epitopes thereon.

The ultimate aim in the construction of the non-immunogenic but suppressive molecule central to this invention involves covalent linkage of a sub-immunogenic number of haptens, epitopes or proteins containing epitopes, to a carrier molecular scaffolding. A molecular entity will be thus created, capable of exhibiting on its exterior, a sub-immunogenic number of closely spaced ($\approx 100$ Å apart) haptenic or epitope groups capable of binding non-productively to B-cell surface immunoglobulin receptors.

The method for measuring effectiveness of suppression depends on the ability to measure decrease in circulating specific antibody concentration or (if possible, as in animal models), decrease in the number of antibody-secreting plasma cells. One of the advantages in the application of this invention is that it enables one to use extremely small (e.g. 0.5 mgs/kg) quantities of administered suppressive molecules. This brings the dosage into pharmacologic range and greatly minimizes problems of toxicity.

The invention is illustrated by the suppression of an ongoing anti-Dnp antibody response by appropriate non-immunogenic Dnp polyacrylamide molecules, as previously described.

As other examples of the use of the invention, there may be mentioned the following:

(1) Suppression of Allergy to Pollen

Pollen may be fractionated to separate the major immunogenic protein materials in relatively pure form. This material may then be used to construct sub-immunogenic molecules by one or more of the following procedures:

(a) The protein may be covalently linked (e.g. by an amide bond between carboxyl and amino groups) to a carrier backbone polymer such as linear polyacrylamide or to a liposome.

(b) The epitope-containing pollen protein may be cross-linked to itself (e.g. using linking agents such as disuccinimidyl suberate) to form soluble "micro-grains" exhibiting a sub-immunogenic number of epitopes on their exterior surface. This would form a homogeneous "micro-grain" structure. Such a structure is possible only if the constituent proteins are soluble in physiological saline.

(c) If the epitope-containing pollen protein is insoluble, it may be solubilized with mild detergent (e.g. Triton-X-100), and cross-linked to a suitable soluble protein carrier (e.g. human serum albumin or human immunoglobulin). This would form heterogeneous "micro-grains".

(2) Suppression of Auto-Immune Disease

This is dependent on the ability to identify the self-antigen being reacted against. For example, such self-antigens have been identified in myasthenia gravis and multiple sclerosis.

(a) Multiple Sclerosis

Auto-antibodies against myelin basic protein have been implicated in this disease. To construct suppressive molecules, one would synthesize sub-immunogenic molecules containing myelin basic protein as described above for pollen proteins.

(b) Myasthenia Gravis

Auto-antibodies against acetylcholine receptors of the neuro-muscular junction have been implicated in this disease. Again, one would proceed to construct suppressive molecules using one of the procedures described above, depending on which one is found to be most appropriate.

(3) Suppression of response to an antigen where those parts of the molecule acting as epitopes are chemically defined If it is known that only certain portions of the molecule stimulate antibody production (e.g. subsections of the myelin basic protein) it may be possible to chemically synthesize these polypeptide regions. One would then create sub-immunogenic (suppressive) molecules by covalently attaching these polypeptides to synthetic polymers or alternately by covalently attaching them to small cross-linked clusters of human serum albumin molecules or to liposomes.

DISCUSSION OF THE THEORY OF THE INVENTION

To further describe the invention there are given below the results obtained in using size-fractionated Dnp-polyacrylamide preparations in two kinds of experimental procedures: (i) measurement of the shape of the dose-response curve as a function of the dose of polymer as administered in vivo and in vitro and (ii) assessment of the inhibitory effect on the response to immunogenic polymers caused by the presence of polymers that are not substituted with enough haptens to be immunogenic. These results are consistent with the general theory of primary immune responsiveness to T cell-independent immunogens which is based on the immunon model as described in our 1976 paper. This model assumes that (i) each cell capable of responding to a haptenated T cell-independent immunogen contains a large number of individual hapten receptor molecules on its membrane surface; (ii) close spatial clustering of these receptors results from their sequential binding to appropriately spaced haptens on one immunogenic molecule; (iii) an immunon can be formed, but only very slowly, when the receptor cluster contains the critical number of linked receptors; (iv) the cell will receive a specific stimulus, when sufficient "immunons" have been formed, that initiates a complex and multistep process leading to cell division, cellular differentiation, and antibody production; and (v) the amount of the primary immune response that is induced in an animal not previously exposed to the hapten is directly related to the rate of immunon formation in the population of cells bearing receptors for the hapten.

The kinetic process of immunon formation is symbolized in FIG. 1 in which receptors on a cell surface are shown to be interacting with a molecule of immunogenic or stimulatory polymer S (FIG. 1a) or interacting with a molecule of nonimmunogenic (or nonstimulatory) polymer N (FIG. 1b). Polymer N, which is not capable of causing a specific immune response at any dose because it has an insufficient number of hapten groups, has been found to inhibit strongly the immunogenic effects of polymer S. According to the model, the inhibition is caused by nonproductive competition for binding sites. The essential difference between the immunogenic molecule S and nonimmunogenic molecule N is that the former can bind at least q cell receptor molecules, whereas the latter cannot (where q is the immunon number). The model assumes that once q cell receptors have been bound, the molecular cluster represented by $S_q$ can undergo a slow, irreversible structural transformation with rate constant $k^*$ to form immunons. Theoretical consideration of the differential equations describing the formation of immunons leads directly to a quantitative relationship expressing the immune response as a function of the concentration of immunogenic and non-immunogenic molecules.

From this relationship it has been shown (see our January 1982 paper) that if doses $D_S$ of immunogen and $D_N$ of nonimmunogen are injected into one animal and doses $D'_S$ and $D'_N$ are injected into a second animal, then the ratio r of immune response in the first animal relative to that in the second animal should be given by $$r = \frac{D_S}{D'_S} \left[ \frac{(q-1) D_S^{max} + D'_S + D'_N}{(q-1) D_S^{max} + D_S + D_N} \right]^q \quad [1]$$

where $D_S^{max}$ corresponds to the dose of immunogen giving maximum response in an animal—i.e., the peak of the dose—response curve. The peak of the curve corresponds to optimal occupancy of receptor groups by large molecular clusters. Addition of more immunogenic polymer causes a decrease in the average cluster size. Addition of nonimmunogenic polymer competes nonproductively for receptor sites. In either case, immunon formation is inhibited by nonproductive competitive inhibition. Thus, high-dose suppression by immunogenic polymer and suppression by nonimmunogenic polymer both operate by a common mechanism—competitive inhibition of immunon formation by nonproductive binding of specific receptors.

EXAMPLES

The invention is illustrated by the following examples:

EXAMPLE 1

Linear polyacrylamide substituted with Dnp hapten groups was prepared as described in our abovementioned 1976 paper. Thus, linear polyacrylamide (Gelamide 250-American Cyanamid) with average molecular weight $5 \times 10^6$ was substituted with ethylene diamine in a manner analogous to that previously used for polyacrylamide beads (Inman et al, Biochemistry 8, 4074–4082 (1969). Dnp derivatives were obtained by shaking the ethylene diamine substituted derivatives with excess fluorodinitrobenzene followed by extensive dialysis. The degree of substitution was determined from measurement of dry weight and optical absorbance at 360 nm. Preparations were labeled with $^{125}I$ substitution levels of approximately one per 2500 monomer units were obtained, corresponding to less than one $^{125}I$ per molecule labeled.

Dnp-substituted polymers were fractionated by gel filtration through 1 m long columns of Bio-Gel A-0.5M agarose beads. These original fractions were further fractionated three more times to obtain relatively homogeneous preparations, as determined by sedimentation equilibrium measurement in the analytical ultracentrifuge.

Two Dnp-substituted polymer preparations were obtained having the following characteristics:

|  | Polymer B | Polymer D |
|---|---|---|
| Molecular weight, $\times 10^{-5}$ | 0.8 | 1.8 |
| Acrylamide monomer subunits/molecule | 1050 | 2350 |
| Extended length of polymer chain, A | 2600 | 6000 |
| Acrylamide monomer subunits/Dnp | 42 | 36 |
| Average distance between Dnp groups, A | 105 | 90 |
| Total Dnp groups/molecule | 25 | 66 |
| "Effective" Dnp groups/molecule | 8–12 | 22–33 |

Polymer B was not immunogenic while Polymer D was (see Table 1, 1976 paper noted above). p Polymers B and D were subjected to further column fractionation on Sepharose C1-4B. Two preparations (N and S) were separated for further testing. Preparation N was a central subfraction of polymer B and preparation S was a central sub-fraction of polymer D. Measurement of partial specific volume (0.690 ml/g) and extrapolation of sedimentation equilibrium molecular weight to zero concentration gave values of 60,000 for N and 130,000 for S. These values together with dry weight and absorbance at 360 nm show N to contain 19 Dnp groups per molecule [7-9 "effective" or appropriately spaced] whereas S contains 43 Dnp groups per molecule (14–21 "effective"). Polymers N and S had almost identical "epitope densities" or degrees of substitution by hapten per molecular size unit.

Antibody Response

Polymer preparations were injected intraperitoneally in BALB/c mice in 0.5 ml of isotonic saline. After 6 days, blood was collected by bleeding from the tail, and the serum was stored at $-30°$ C. until analysis. The concentration in serum of IgM antibody against Dnp was determined by a solid-phase binding assay. Surfaces covalently coated with Dnp-substituted gelatin served to bind the anti-Dnp mouse antibody, whose presence was then measured by a second incubation with $I^{125}$-labeled rabbit antibody against mouse IgM antibody.

In vitro Culture and Assay

Mice were killed by cervical dislocation, and their spleens were minced in RPMI-1640 medium and pressed through a stainless steel mesh (60×60 mesh; 0.019-cm diameter). Cellular debris was allowed to settle, and the supernatant containing a dispersed-cell suspension was decanted, freed of erythrocytes by osmotic shock, and washed. Suspensions of nucleated spleen cells were then incubated with or without appropriate polymer in 60×15 mm tissue culture dishes containing $5 \times 10^7$ viable cells in a final volume of 7.5 ml. The incubation was carried out in 5% $CO_2$/95% water-saturated air at 37.0° C. The incubation medium consisted of RPMI 1640 medium enriched with 5% (vol/vol) heat-inactivated fetal calf serum, 2% (vol/vol) heat-inactivated horse serum, 4 mM glutamine, 100 units of penicillin and 100 μg of streptomycin per ml, and 50 μM 2-mercaptoethanol.

After 3 days of incubation, cells were harvested and washed. Assay for direct (IgM) anti-Dnp plaque-forming cells was performed.

Figure 2:
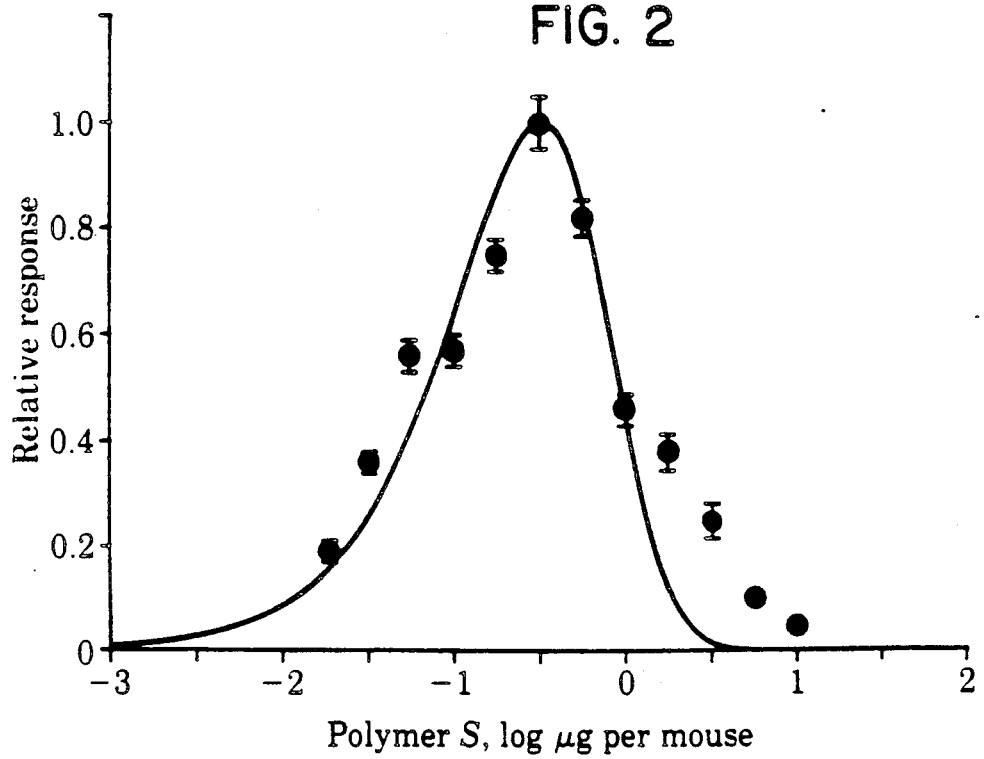

The immunological response in BALB/c mice 6 days after injection of various doses of immunogenic polymer preparation S, as measured by the concentration of serum IgM molecules reactive toward Dnp groups, is shown in FIG. 2. The mice in this experiment came in a single shipment of uniform age from the supplier and were divided into groups of 10. Members of each group were injected with the same dose, and all groups were handled as uniformly as possible. The solid curve in FIG. 2 is the theoretical response curve expected from Eq. 1 as visually fitted to the experimentally determined points by adjustment of the numerical value of $D_s^{max}$ to 0.3 μg. In view of the simplicity of the assumptions involved in the derivation of Eq. 1 and the known variability of response of individual mice, the agreement between theory and experiment is surprisingly good. However, when the experiment was repeated by using different groups of mice supplied by the same breeder, the variability of biological responses in whole animals became more evident.

Figure 3:
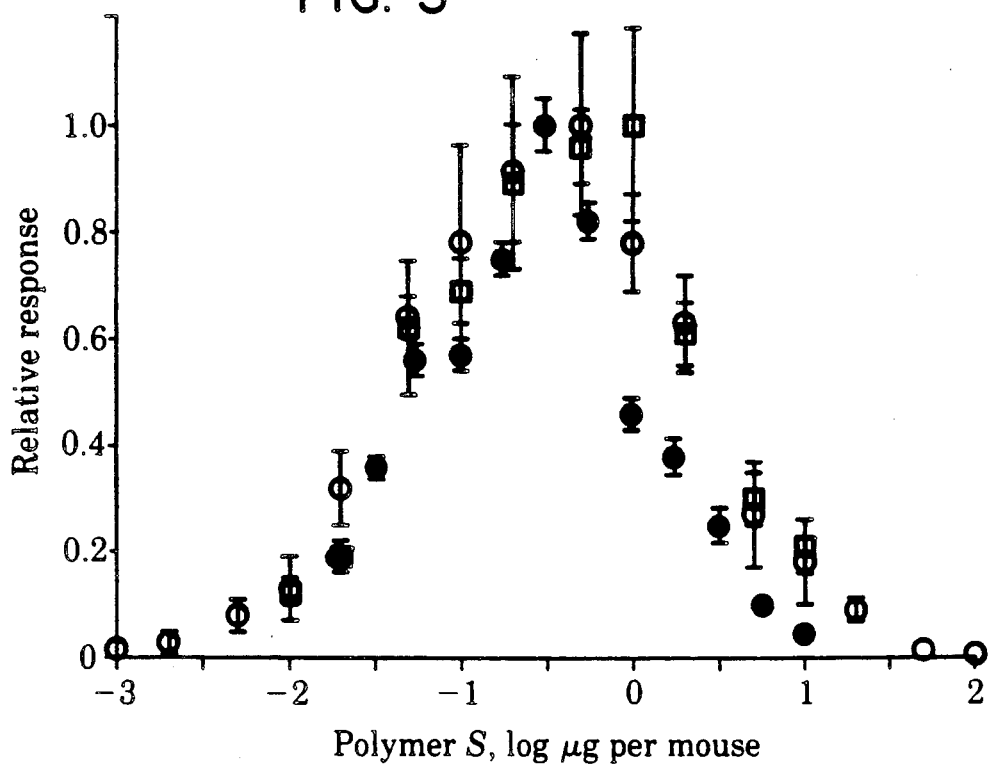

FIG. 3 compares the dose-response curves of three separate shipments of BALB/c mice and illustrates both group-dependent variability of response of individual mice at each dose and some change of shape of the dose-response curve from group to group. The variable immunological response given by different groups of mice is a well-known phenomenon, having been observed both in studies using whole animals and in those using cell cultures. It probably is dependent on factors in the previous history and handling of the animals, such as exposure to bacteria, viruses, and parasites, which might influence the "antigenic naivete" of the animals, as well as exposure to environmental shocks such as heat and cold during shipment.

By comparing the observed dose-response curves shown in FIGS. 2 and 3 with the theoretical curve shown in FIG. 2, it is clear that although the agreement between curves is good, the observed responses are quite variable from one batch of mice to another and, in general, show a wider dose-response curve than expected from the simple model that generated the curve shown in FIG. 2.

The wider experimental curve may be explained in the following way:

The theoretical curve in FIG. 2 is based on the assumption that all cells responding to the immunogen have receptor molecules with the same binding constant for Dnp groups. This assumption of complete homogeneity is unlikely to be true. If cells that bind immunogen and respond to it have protein receptors with differing binding constants for Dnp, then the predicted response should be the sum of a number of individual cellular response curves. Each curve would be like that in FIG. 2, but those with lower binding constants would be displaced to the right by an amount proportional to the ratios between their binding constants for Dnp. Inspection of FIGS. 2 and 3 from this point of view indicates that the observed width of the experimental dose-response curves may be understood as resulting from the summation of responses from individual populations of cells having receptors differing in binding constants by 1–1.5 log units—i.e., 10- to 30-fold. The dose-response measurements can be fit within experimental error by summing the theoretical responses of three or four such populations.

Figure 4:
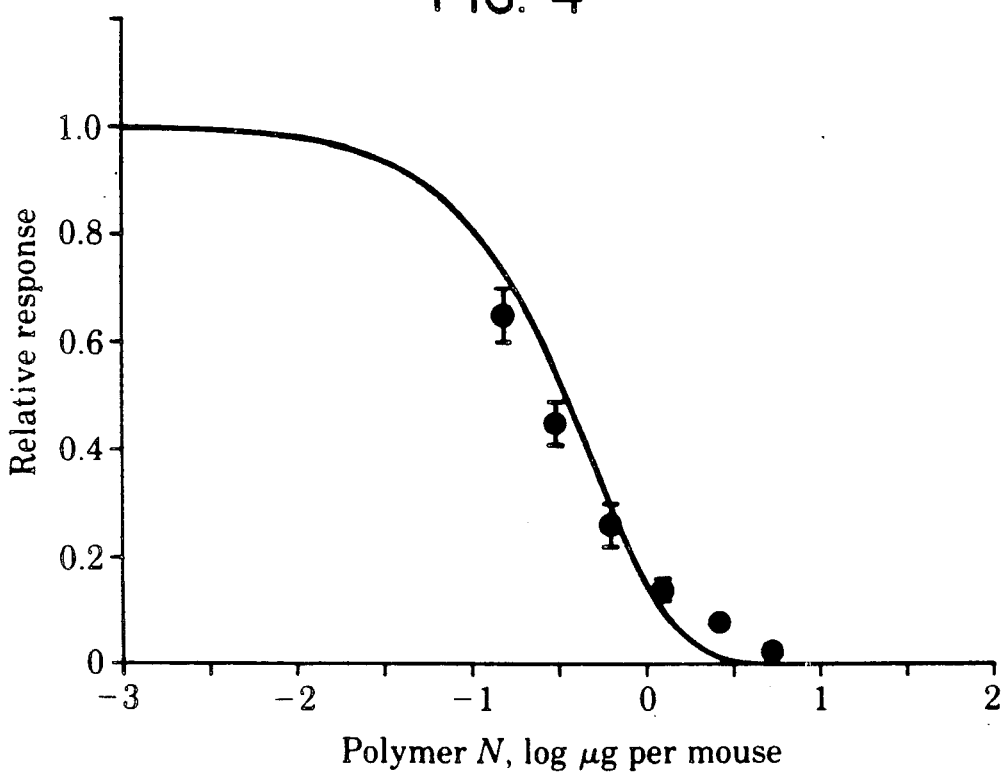

For a constant dose of immunogenic polymer, Eq. 1 also can be used to predict the extent of reduction of response that will be obtained with doses of increasing amounts of nonimmunogenic polymer N. Measurements of this type are shown in FIG. 4 for BALB/c mice. The solid line in FIG. 4 is not fitted to the data but is calculated directly from Eq. 1 by using the estimated value of the maximum-response dose $D_s^{max}$ of 0.5 μg per mouse obtained from FIG. 3. The agreement between the experimental points and the calculated theoretical curve in FIG. 4 is remarkable, if one considers the absence of arbitrarily adjusted parameters in this calculation.

Figure 5:
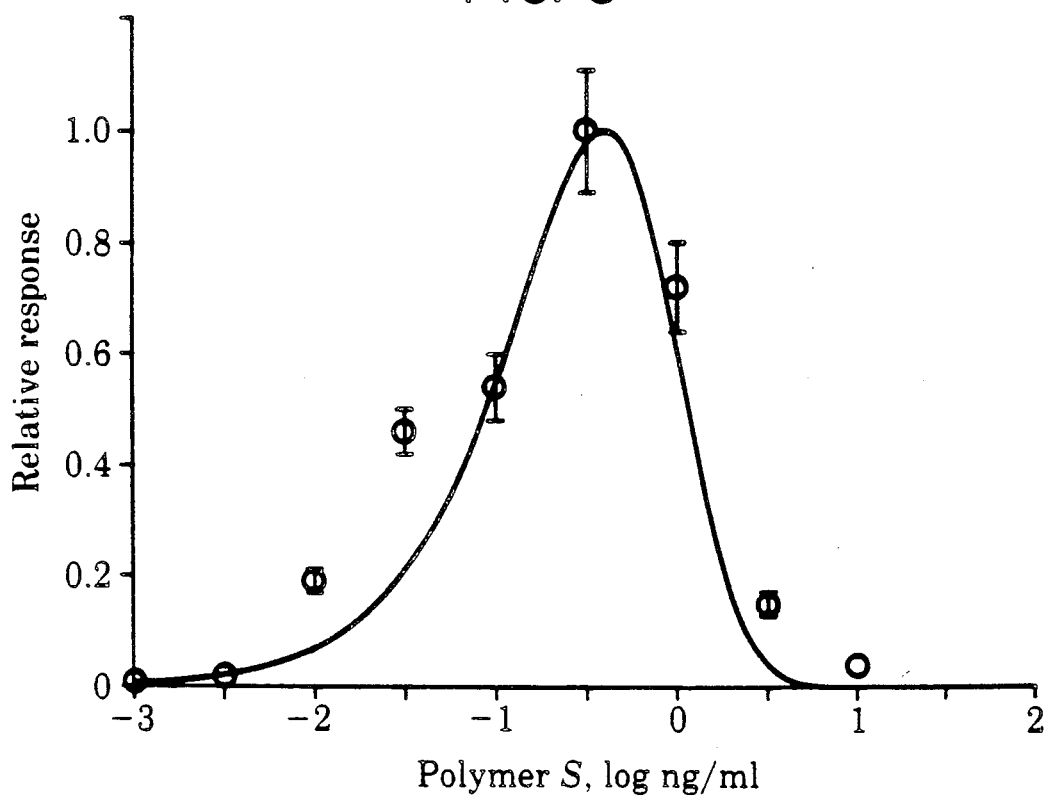

In addition to experiments in living animals shown in FIGS. 2, 3, and 4, dose-response curves were measured in vitro with isolated mouse spleen cells. FIG. 5 shows the results of such an in vitro experiment as compared with a visually fitted theoretical curve calculated from Eq. 1. The agreement between experiment and theory for the in vitro experiment with cultured spleen cells (FIG. 5) is approximately as good as it was for the in vivo experiment with whole mice (FIG. 2). In both cases, the measured response curve is somewhat broader than that predicted from a model based on a homogeneous hapten binding constant in the responding cells.

Figure 6:
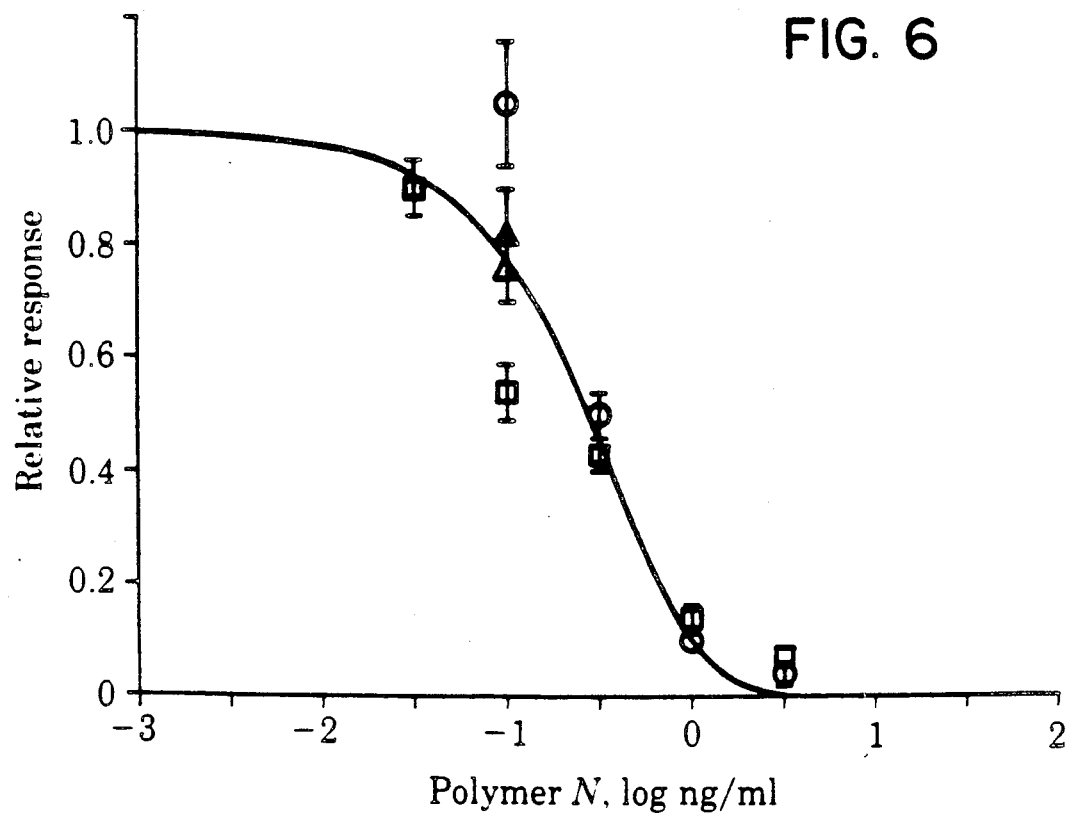

Of particular significance to the present invention are measurements of the inhibition of immune response in vitro with increasing amounts of nonimmunogenic polymer which are shown in FIG. 6. The solid line is not fitted to the data but is calculated directly from Eq. 1 by using the estimated value of the maximum-response dose, $D_s^{max}$, of 0.4 ng/ml from FIG. 5. There is substantial agreement between the experimental points and the calculated theoretical curve.

The blood volume and extracellular fluid volume of a mouse are each $\approx 1$ ml, so the optimal immunogenic polymer dose in vivo is $\approx 1$ μg/ml. There is a large apparent discrepancy between this in vivo dose and that which is Optimally immunogenic in vitro ($\approx 1$ ng/ml). The almost 1000-fold sensitivity difference is largely explained by rapid removal in vivo of polymer molecules by phagocytes located throughout the body. Studies with $^{125}$I-labeled preparations of the polymers as described in our 1976 paper showed that the bulk of the injected polymer is quickly removed from the circulation by Kupffer cells in the liver and phagocytic cells in other tissues. The resulting rapid fall in free polymer concentration, coupled with uncertainties concerning the rate of equilibration of polymer between different body fluid compartments makes difficult any quantitative comparison of relative optimum concentrations in vivo and in vitro. In spite of these difficulties, there remains the fact that the shapes of the dose-response and dose-suppression curves measured in vivo are remarkable similar to those measured in vitro, implying strongly that the same limiting process is being probed in both cases. Furthermore, in both cases the measured responses as a function of dose are in excellent agreement with values obtainable from Eq. 1.

Although polymer N fails to stimulate at any dose, it inhibits polymer S at the same dose where polymer S is maximally stimulatory. This indicates a competition for surface receptors. Because both polymer preparations have almost identical "epitope densities" with a common carrier chemistry, this finding is in disagreement with theories that explain immunogenicity by invoking epitope density or polyclonal (i.e., nonspecific) activation by the "carrier".

DISCUSSION OF EXAMPLE 1

The data presented above indicates the following with regard to a specific T cell-independent stimulus: (i) a specific immunogenic signal is generated by the formation of immunons on the surface of a responsive cell, (ii) an immunon will form only after a sufficient number of surface receptors are clustered, and (iii) specific clustering of surface receptors occurs as a consequence of their being bound to linked haptens. This binding is specific for the hapten-receptor interaction and does not primarily depend on the "scaffolding" to which the haptens are attached. The underlying physical scaffold that links the haptens may be molecular in nature or may consist of a surface on which small hapten-containing structures are aggregated, as on the surface of an "antigen-presenting cell."

Nonspecific stimuli, such as mitogens, lectins, antibodies against cell surface proteins, and activating or inhibiting factors from other cells, may well influence the level of "irritability" of the responding cell, making it more or less likely to respond to a given amount of immunogenic signal or even to respond in the absence of specific signals. Factors from T cells and macrophages have previously been shown to enhance antibody responses nonspecifically. Mitogens are known to stimulate cells nonspecifically to secrete antibodies. Whether or not they do this directly or indirectly by a mechanism involving specific receptor aggregation is not known. However, in contrast to these nonspecific stimuli, the data herein indicates that specific stimulation occurs by means of the linkage of receptors by their specific binding sites into immunons; thus, cells displaying those receptors are stimulated to divide and differentiate into cells that will secrete specific antibodies.

It has been demonstrated above (and in our 1976 and 1982 papers) that molecules consisting of haptens linked to a flexible linear polymer are immunogenic only if they have a sufficient number of adequately spaced haptens. This finding with a T cell-independent antigen might at first seem contradictory to the fact that many protein molecules that are T cell-dependent antigens and which do not contain multiple identical antigenic sites are nevertheless antigenic. However, several studies have shown that the antigenicity of proteins in vivo depends on their state of aggregation. It is well-known that experimentally induced aggregation of protein molecules by physical methods (heat, adsorption to bentonite, emulsification with Freund's adjuvant) or by chemical methods (cross-linking with glutaraldehyde or alum) greatly enhances their antigenicity. Nonaggregated protein molecules centrifuged free of aggregates or collected from the sera of injected animals have been shown to be not immunogenic but tolerogenic, whereas aggregated material with presumed multiple antigenic sites produces an immune response. Therefore, it is possible that the minimum requirements for antigenicity as determined with simple T cell-independent polymer may have applicability to immune responses to a large variety of molecules, including T cell-dependent ones. It is in any case evident that the suppressive effect of the nonimmunogenic polymer, on the immunogenic polymer, as illustrated above, can be used to control undesired immune response. The amount of non-immunogenic polymer so used will necessarily vary depending on the specific immune response which is involved, the polymer carrier, the effective number of epitopes involved, body weight and other factors. It is believed, however, that the administration of from 0.5 to 50 mg/kg body weight would be effective in controlling undesired immune response. The administration may be effected by, for example, injection using a sterile solution of the non-immunogenic polymer.

EXAMPLE 2

Treatment of Multiple Sclerosis

An autoimmune response to myelin basic protein is believed to be a prime factor in the generation of the disease, multiple sclerosis. To generate a disease in mice comparable to the human disease, a number of mice can be stimulated to make antibody against myelin basic protein by injection with that protein in complete Freund's adjuvant. After a number of days, when antibodies have been formed and disease symptoms appear, a portion of the mice can also be injected with a nonimmunogenic polymer comprising a polyacrylamide carrier as used in Example 1 with a number (e.g. 6–10) of epitopes of myelin basic protein spaced along the polymer chain.

After an appropriate time, e.g., a few weeks, all of the test mice can then be sacrificed and examined for damage to nervous tissue and level of antibody. The amount of antibody and the extent of nervous tissue damage in the mice treated with nonimmunogenic polymer should be substantially less than that in the mice not so treated.

EXAMPLE 3

Treatment of Myasthenia Gravis

Antibody mediated mechanisms are believed to be responsible for impairing neuromuscular transmission in the disease myasthenia gravis. The culpable antibody reacts against acetyl-choline receptors (AChR) at the neuromuscular junction. Mice given an injection of purified acetyl-choline receptor in Freund's adjuvant and pertussis as additional adjuvant develop muscular weakness and fatigability characteristic of myasthenia gravis. Mouse acetyl-choline receptor can be purified from mouse muscle by the use of affinity chromatography columns containing $\alpha$-bungerotoxin. Once the experimental disease has been developed in mice, a portion of them can be "treated" by injection of a nonimmunogenic polymer comprising a polyacrylamide polymer substituted with 6-10 AChR, or effective portions thereof, per molecule. The "cure" of test mice can be followed by measurement of decrease of level of high affinity AChR antibody in the serum of treated mice as compared with level and affinity of AChR antibody in control (or untreated) mice.

In lieu of the polyacrylamide carrier, an appropriately sized liposome (e.g. 300A) could be used to carry the indicated 6-10 AChR, or effective portions thereof, on its exterior surface.

EXAMPLE 4

Treatment of Autoimmune Thyroiditis

This disease, characterized by a lymphocytic infiltration of the thyroid and interference with normal thyroid function, is believed to be caused by an autoimmune mechanism whereby antibodies to thyroglobulin are formed.

The disease can be simulated in mice by injection of thyroglobulin in complete Freund's adjuvant. Within a number of days, the thyroid can be seen to be inflamed and infiltrated with lymphocytes; the severity of the disease is proportional to this infiltration.

The proposed "cure" will be elicited by injection of thyroglobulin oligomers. These can be produced by appropriate cross-linking of tetrameric thyroglobulin molecules into sub-immunogenic conjugates of approximately 2-4× the normal molecular weight. The cross-linking can be done as discussed above, using appropriate molecular ratios of di-succinimidyl suberate or equivalent cross-linking agents.

"Cured" animals will exhibit thyroid glands free of lymphocytic infiltrates and absence of circulating antibody molecules against thyroglobulin.

EXAMPLE 5

Treatment of Penicillin Hypersensitivity

Penicillin hypersensitivity is believed to be caused by the combination of tissue proteins with the major penicillin breakdown product: benzylpenicilloyl (BPO). This combination can induce the formation of IgE antibodies against penicillin. These antibodies, in turn, are largely responsible for the induction of symptoms of hypersensitivity when penicillin is administered to sensitized individuals.

The proposed treatment involves chemical construction and injection of appropriate subimmunogenic polymers or liposomes comprising BPO haptenic groups covalently linked to a carrier of polyacrylamide, human immunoglobulin, serum albumin or liposome. Cure can be evidenced by decrease in circulating serum anti-penicillin IgE levels as measured by skin tests (specifically, passive cutaneous anaphylaxis, PCA).

Models of disease induction and cure can be carried out in mice. Penicillin sensitivity can be induced by the administration of 1-10 micrograms of $BPO_3$ ovalbumin absorbed on 1 mg aluminum hydroxide injected intraperitoneally. After 12 days, serum IgE levels rise and remain high for several weeks, as measured by PCA in rats. Cure involves injection of the subimmunogenic polymers described above and will be exhibited by negative PCA results indicating lack of anti-BPO IgE antibodies.

It is contemplated that the invention can be used to treat a wide variety of autoimmune or allergic disorders in addition to those exemplified above, e.g. Graves' disease, insulin resistance, pemphigus or Goodpasture's syndrome.

It will be appreciated that various procedures, understandable to one in the art, may be used to add the desired hapten or epitope to the carrier. For example, epitopes may be covalently bonded to free amino groups of phosphotidyl ethanolamine present on the exterior surface of a liposome used as carrier. Similarly, Dnp groups can be added to a polymer carrier (e.g. polyacrylamide) in the manner described above in Example 1. A more detailed description of the procedure as used to make one gram of polymer substituted about 1/50 with Dnp is given below:

Mix 100 ml of ethylene diamine (EDA) with 50 ml of $H_2O$ and cool to room temperature. Add with rapid stirring 50 ml of a 2% solution of the polymer in water. Heat at 50° C. for 15 minutes, cool rapidly to room temperature and set to dialyze in ⅜ inch dialysis tubing, stirring in large chromatography jar, and changing water early morning and late afternoon for three days. The resulting solution should contain polymer substituted approximately 1/50 with EDA. The polymer is put into 250 ml screw top flasks (approx. 100 ml per flask) and solid $K_2HPO_4$ added to give 0.1M $K_2HPO_4$ (dissolve by shaking in rotary bath at 60° C.). Approx. 0.5 ml flourodinitrobenzene is added to each flask and the flasks shaken vigorously for 2-3 hours at 60° C. During this time the pH will drop slowly from ~9.0 to ~7.5 as the FDNB hydrolyzes and reacts. The solution is then allowed to cool to room temperature and stand overnight during which time a small amount of loose ppt. often forms. The supernatant is decanted into 15 ml centrifuge tubes and spun at top speed in the desk top centrifuge for 10 minutes to remove traces of ppt. The clear supernatant is dialyzed against distilled water (changing 2× daily) until all color stops dialyzing (usually 2 to 3 days).

| EDA Reaction Concentration | Temp of EDA Reaction, °C. | Time of EDA Reaction | Temp. of Dialysis | Substitution Level |
|---|---|---|---|---|
| 50% | Room Temp. | -0- | Coldroom 2-3° C. | 1/110 |
| 50% | 50° | 2 hours | Room Temp. | 1/15 |
| 50% | 50° | 30 min. | " | 1/30 |
| 50% | 50° | 15 min. | " | 1/50 |
| 50% | Room Temp. | 0 | " | 1/67 |
| 25% | " | 0 | " | 1/86 |
| 10% | " | 0 | " | 1/300 |
| 2.5% | " | 0 | " | 1/700 |

While the various drawings accompanying this specification have been referred to above, the following further comments as to the several figures may be useful:

FIG. 1 is a diagrammatic representation of the stepwise assembly of an immunon cluster, Φ. The solid rectangles represent mobile protein receptor molecules containing binding sites (cups). The curved solid lines represent flexible polyacrylamide molecules with attached Dnp groups shown as solid circles. Receptors are shown as reacting stepwise either with an immunogenic polymer, S, or with a nonimmunogenic polymer, N. Subscripts on S and N are used to designate polymer molecules bound to clusters of surface receptors of the specific number designated by the subscript. Polymer N cannot form immunons because it cannot simultaneously bind enough receptors (because $n<q$).

FIG. 2 sets out dose-response measurements showing the mean of the relative concentration, in serum from individual mice, of IgM antibody against Dnp at 6 days after injection of polymer S in amounts shown (10 BALB/c mice per point). Error bars indicate SEM when it is larger than the circle. The solid curve gives the theoretical response expected from Eq. 1 for a peak response occurring at a dose of 0.3 μg per mouse and an immunon size, q, of 10. The theoretical response is not sensitive to the value of q if q is greater than five. The peak of the response curve corresponds to approximately 30 μg of anti-Dnp IgM per ml of serum.

FIG. 3 shows dose-response measurements for different lots of BALB/c mice. Measurements were made on serum from individual mice. The mean of measurements on each group at each dose is shown, together with the SEM when it is larger than the symbol. Of the symbols used, the solid black dot represents ten mice per point (these points being the same as in FIG. 2); the open circle "○" represents five mice per point; and the symbol □ represents six mice per point.

FIG. 4 shows response-reduction measurements for increasing doses of nonimmunogenic polymer preparation N injected simultaneously with a constant dose of immunogenic polymer preparation S. Measurements were made on serum from individual mice. The mean of each group is shown together with the SEM when it is larger than the symbol. BALB/c mice, 10 mice per point; 0.31 μg of polymer S given to each mouse. The solid curve gives the theoretical response expected from Eq. 1 for an immunon size, q, of 10 and $D_S^{max}$ set equal to 0.5 μg per mouse as derived from FIG. 3. The theoretical response is quite insensitive to the value of q but is shifted left or right according to the value of $D_S^{max}$, with no change in shape.

FIG. 5 shows dose-response measurements regarding the relative number of direct anti-Dnp plaques produced from spleen cell cultures 3 days after the start of incubation in the presence of various concentrations of immunogenic polymer S. The data represent the mean of duplicate cultures with triplicate assays per culture; the SD is indicated when it is larger than the circle. The experimental peak response corresponds to ≈300 plaques per $10^6$ spleen cells with a blank (without polymer) of ≈20 plaques per $10^6$ spleen cells. The curve gives the theoretical response expected from Eq. 1 for a peak response occurring at a polymer concentration of 0.4 ng/ml and an immunon size, q, of 10.

FIG. 6 shows dose-reduction measurements for increasing doses of nonimmunogenic polymer preparation N incubated in spleen cell culture with a constant dose (0.3 ng/ml) of immunogenic polymer preparation S. Procedures and data treatment were as in FIG. 5. The different symbols show data obtained in separate experiments. The solid curve gives the theoretical response expected from Eq. 1 for an immunon size, q, of 10 and $D_S^{max}$ set equal to 0.4 ng/ml as derived from FIG. 5.

Vaccine Embodiment

The invention also includes, as an extension of the finding that nonimmunogenic polymer will suppress immunogenic polymer, the feature of improving the effectiveness or efficacy of vaccines by removing, or avoiding in the case of new vaccines, nonimmunogenic polymers. Many vaccines are derived from bacterial or virus products comprising mixtures of polymers of varying molecular weights. According to the invention, low molecular weight polymers can be sub-immunogenic and suppressive of the response to polymers of higher molecular weight. Accordingly, the present invention proposes to optimize the effectiveness of vaccines in one of the following ways:

(1) From a naturally occurring polymeric immunogen (e.g. pneumococcal polysaccharide type III), sub-immunogenic smaller polymers would be removed because they act to inhibit the immune response against larger polymers. Thus, for example, vaccines against bacterial pneumonia, according to the invention, would contain only immunogenic molecules of molecular weight no lower than 250,000.

(2) If naturally derived materials are not effective as vaccines (e.g. the polysaccharide of hemophilus influenza type B, or protein toxoids) the invention contemplates increasing effectiveness by polymerizing the material into molecules containing more than the threshold number of epitopes.

The polymerization process can be one of the following:

(a) self-polymerization by co-valent bond formation;

(b) covalent bonding to a synthetic polymer carrier; or (c) covalent bonding to polymerized human protein such as serum albumin. In all of these embodiments or modifications, the essential feature is to provide a vaccine which contains immunogenic polymers but which has been so processed as to be free from suppressive polymers. This insures that the resulting vaccine will be as effective as possible by eliminating or avoiding the non-effective and suppressive polymeric materials. Fractionation of existing vaccines to remove low molecular weight non-immunogenic polymer can be accomplished using conventionally available techniques to up-grade existing vaccines or in making new ones.

Examination of three lots of pneumococcal polysaccharide Type III vaccine from commercial sources show that these contain polymers of varying molecular weight including a substantial amount of polymer in the order of 70,000 and lower. Removal of this lower molecular weight polymer so that the vaccine essentially contains only polymer of 250,000 molecular weight or above should improve the effectiveness of the vaccine. This is based on the concept that the lower molecular weight polymers are essentially nonimmunogenic but compete for receptor sites with the higher molecular weight immunogenic polymer and thus suppress the action of the latter. It is further noted in this regard that the use of too much immunogenic polymer can also have a suppressive effect due to competition for receptor sites which limits the desired immunon formation. Hence, it is important not only to avoid the presence of low molecular weight non-immunogenic polymers in vaccines but to determine the optimum amount for most effective use. This is especially true for young people.

SUMMARY OF THE INVENTION

In summary, the invention contemplates, in one of its embodiments, administering, e.g. intravenously, a nonimmunogenic material which competes with immunogenic material and prevents the latter from triggering undesired antibody formation. It will be appreciated that the antibody production is eliminated or inhibited by suppressing the stimulation of the progenitor or precursor cells, rather than inhibiting the secretion of antibodies by plasma cells which are the progeny of the precursor cells. Plasma cells differentiate from stimulated precursor B-cells with receptors. It is the stimulation of the latter which is suppressed, according to one embodiment of the invention, by preventing the essential immunon formation through competition for cell receptors between immunogenic and nonimmunogenic material.

The further embodiment of the invention contemplates improving the effectiveness of vaccines by eliminating the nonimmunogenic material which is competitive with the effective immunogenic material.

Various modifications may be made in the invention as described above. Accordingly, the scope of the invention is defined by the following claims wherein:

We claim:

1. A method of specifically suppressing an undesired immune response in a mammal, where said response is caused by antibody production of B-lymphocytes in response to introduction of a T-cell independent antigen into said mammal, wherein the method comprises:

(a) preparing a construct comprising at least one discrete antigenically recognizable moiety bound to a non-immunogenic pharmacologically acceptable carrier, wherein said moiety corresponds to an antigenic determinant of said T-cell independent antigen causing the undesired immune response, and wherein the number of said moeities bound to said carrier and the spacing of said moeities on said carrier are such that said construct does not elicit an immune response to said moeities but does directly compete with said T-cell independent antigen for receptors on said B-lymphocytes, and thereby said construct specifically suppresses said undesired immune response; and (b) administering said construct to said mammal in an amount such that suppression of said undesired immune response is effected.

2. The method of claim 1, wherein the construct comprises 8–10 haptens or epitopes spaced 100–200 Å apart along the carrier.

3. The method of claim 1 wherein the antigen is an allergen or a autoimmune-antigen which, respectively, causes an allergic reaction or an autoimmune disease.

4. The method of claim 1 wherein the non-immunogenic carrier is selected from the group consisting of naturally derived or synthetic polymers, proteins and liposomes.

5. The method of claim 1 wherein the carrier is a protein normally occurring in the mammal which is treated.

6. The method of claim 5 wherein the carrier is human serum albumin or immunoglobulin.

* * * * *